United States Patent [19]

Menard

[11] Patent Number: 5,453,143
[45] Date of Patent: Sep. 26, 1995

[54] METHOD OF ATTACHING ADHESIVE TO A TABBED ABSORBENT ARTICLE

[75] Inventor: Michael J. Menard, Doylestown, Pa.

[73] Assignee: McNeil-PPC, Inc., Milltown, N.J.

[21] Appl. No.: 329,137

[22] Filed: Oct. 24, 1994

Related U.S. Application Data

[63] Continuation of Ser. No. 946,989, Sep. 17, 1992, abandoned.

[51] Int. Cl.⁶ ............................. A61F 13/15; A61F 13/60
[52] U.S. Cl. ........................ 156/204; 156/227; 156/289; 156/291; 604/387; 604/389; 604/390
[58] Field of Search ..................................... 156/289, 204, 156/227, 290, 291; 604/387, 389, 390

[56] References Cited

U.S. PATENT DOCUMENTS

| | | | |
|---|---|---|---|
| 3,595,237 | 7/1971 | Sargent et al. | 604/387 X |
| 4,285,343 | 8/1981 | McNair. | |
| 4,576,597 | 3/1986 | Hlaban | 604/389 X |
| 4,589,876 | 5/1986 | Van Tilburg. | |
| 4,596,570 | 6/1986 | Jackson et al.. | |
| 4,605,405 | 8/1986 | Lassen. | |
| 4,615,696 | 10/1986 | Jackson et al.. | |
| 4,701,178 | 10/1987 | Glaug et al.. | |
| 4,846,829 | 7/1989 | Lloyd | 604/389 |
| 4,900,320 | 2/1990 | McCoy | 604/387 |
| 4,911,701 | 3/1990 | Mavinkurve. | |
| 5,133,704 | 7/1992 | Wheeler | 604/390 X |
| 5,330,461 | 7/1994 | Leeker | 604/389 X |

FOREIGN PATENT DOCUMENTS 0313426  4/1989  European Pat. Off. ............... 604/387

*Primary Examiner*—Jeff H. Aftergut

[57] ABSTRACT

A method for making an absorbent article, such as a sanitary napkin, having tabs. A first series of patches of a hot melt type pressure sensitive adhesive are applied to one side of a double-sided release strip. The release strip is then placed against the central portion of the absorbent article so that the first adhesive patches bond to the central portion. A second series of patches of the adhesive are applied to the other side of the double-sided release strip and tabs are folded over the central portion so that the second adhesive patches bond to the tabs. Since the release strip has been coated with a release agent, such as silicone, on both of its sides, the first and second patches of adhesive bond to the central portion and the tabs, respectively, with greater tenacity than they did to the release strip. When the user removes the release strip prior to use, the first and second adhesive patches remain on the central portion and the tabs. Thus, a hot melt type of pressure sensitive adhesive is applied to the central portion and the tabs without danger that they will be scorched by the heat of the hot melt adhesive as it leaves the glue gun.

17 Claims, 3 Drawing Sheets

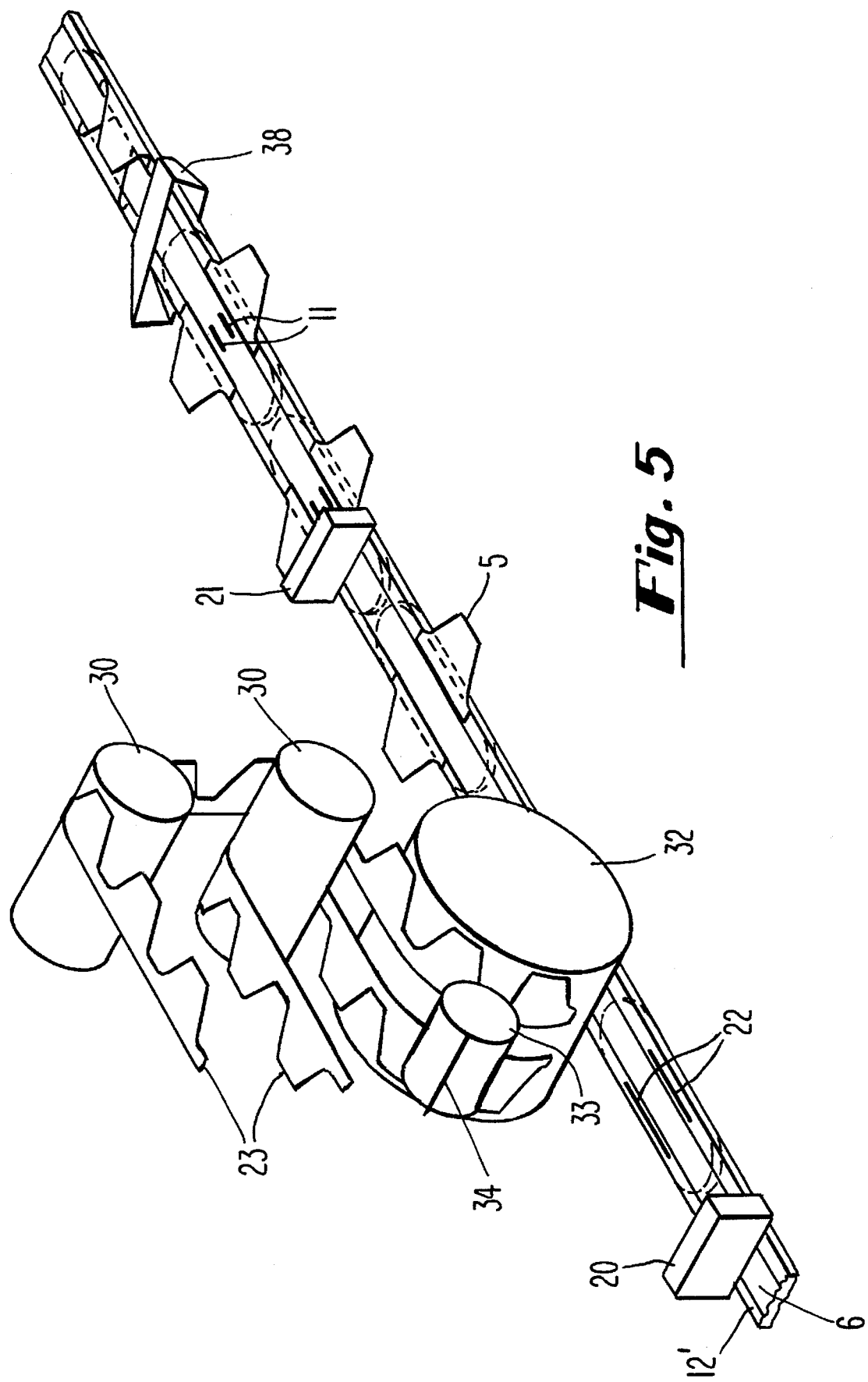

METHOD OF ATTACHING ADHESIVE TO A TABBED ABSORBENT ARTICLE

This is a continuation of application Ser. No. 07,946,989, filed Sep. 17, 1992, now abandoned.

FIELD OF THE INVENTION

The current invention concerns a method of making absorbent articles. More specifically, the invention concerns a method of applying a pressure sensitive adhesive, such as a hot melt glue, to a tabbed absorbent article designed to be worn in the perineal area of the body, such as a sanitary napkin, an incontinence pad or the like.

BACKGROUND OF THE INVENTION

Traditionally, absorbent articles have included a central absorbent portion having a body facing side, a garment facing side, longitudinally extending edges and transverse ends. These articles generally include an absorbent core made of loosely associated hydrophilic materials such as wood pulp. Such products are held in place by providing patches of pressure sensitive adhesive, typically a double sided tape or a hot melt type glue, on the garment facing side that adheres it to the inner crotch surface of the wearer's undergarment.

One drawback of traditional absorbent articles has been that their shape tends to deform during use, thereby allowing the article to move out of position so as to reduce its effectiveness. Subsequent designs have addressed this problem by including tabs or wings that extend laterally from the longitudinal edges of the central portion and wrap around the edges of the undergarment. See U.S. Pat. Nos. 4,285,343 (McNair); 4,589,876 (Van Tilburg); and 4,911,701 (Mavinkurve).

One problem with using such tabbed articles arises due to the fact that the adhesive patches that attach the article to the user's undergarment are typically applied to both the tabs and the central portion. These adhesive strips are often covered with separate protective release strips that protect the adhesive from dirt and unintended adhesion during manufacture, packaging and storage. These release strips must be removed by the user just prior to application of the product to an undergarment.

Unfortunately, multiple adhesive patches and release strips make the application of the article to the undergarment a cumbersome process. Specifically, the user must remove all three release strips (one on the central portion and one on each of the tabs) while simultaneously making sure that the tabs do not inadvertently adhere to one another or to another part of the product. Thus, the user must carefully handle the product when removing the release strip on one tab in order to avoid inadvertently contacting the exposed adhesive on the other tab and the central portion, thereby rendering the product useless. Even when the problem of undesired adhesion is avoided, the user is presented with the task of disposing of three release strips.

Consequently, absorbent articles have been developed that incorporate a single, "double-sided" release strip—that is, a release strip coated on both sides with silicone or the like. The single, double-sided release strip protects the adhesive patches on both the central portion and the tabs, so that a single pull of a release strip is sufficient to prepare the article for application—see U.S. Pat No. 4,701,178 (Glaug et al.). Absorbent articles incorporating this feature are manufactured by applying pressure sensitive adhesive directly to the layers covering the garment facing sides of both the central portion and each of the tabs of the article. A double-sided release strip is then applied to the adhesive on the central body portion and the tabs are folded over the release strip so that the release strip is sandwiched between the adhesive on the central portion and the adhesive on the tabs.

Unfortunately, experience has shown that it is very difficult to apply a hot melt adhesive directly to the layers covering the garment facing side of the central portion and the garment facing sides of the tabs. The difficulty arises because the high temperature of such adhesive as it exits the glue gun can result in scorching of the material from which these layers are formed. As a result, double faced adhesive tape, although more expensive than hot melt glue, has typically been used as the tab adhesive.

Consequently, it would be desirable to provide a method of utilizing hot melt type pressure sensitive adhesive on a tabbed absorbent article, using a double sided release strip to protect the adhesive on both the tabs and the central portion of the article, in such a manner that the application of the adhesive does not result in scorching of the layers covering the article.

SUMMARY OF THE INVENTION

Accordingly, it is the object of the current invention to provide a method of utilizing hot melt type pressure sensitive adhesive on a tabbed absorbent article, using a double sided release strip to protect the adhesive on both the tabs and the central portion of the article, in such a manner that the application of the adhesive does not result in scorching of the layers covering the article. This object, as well as other objects, is accomplished in a method of making an absorbent article comprising the steps of (i) forming a central portion having an absorbent element, (ii) depositing a first patch of adhesive on a first side of a strip of a first material, (iii) placing the first side of the strip on the central portion so that the first patch of adhesive bonds to the central portion more tenaciously than the first patch of adhesive bonded to the strip, (iv) depositing a second patch of adhesive on a second side of the strip, and (v) placing a tab on the second side of the strip so that the second patch of adhesive bonds to the tab more tenaciously than the second patch of adhesive bonded to the strip, whereby the first and second patches of adhesive remain on the central portion and the tab, respectively, when the strip is removed from the article.

In the preferred embodiment, the adhesive comprises a pressure sensitive hot melt glue and the strip of material comprises a double-sided release paper.

BRIEF DESCRIPTION OF THE DRAWINGS

FIG. 5 is a view, partially schematic, of an alternative manufacturing line for making an absorbent article having cut and paste tabs.

DESCRIPTION OF THE PREFERRED EMBODIMENT

Figure 1:
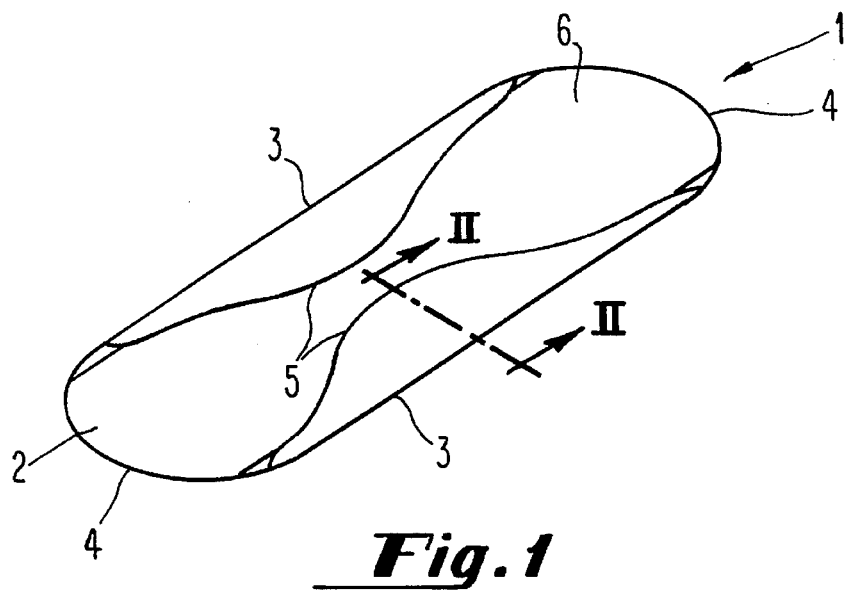
FIG. 1 is an isometric view of an absorbent article made by the method of the current invention, as delivered to the user.
Figure 2:
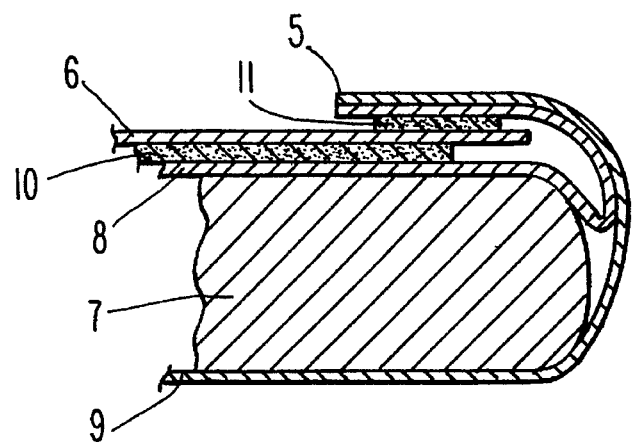
FIG. 2 is a cross-section through lines II—II shown in FIG. 1.
Figure 3:
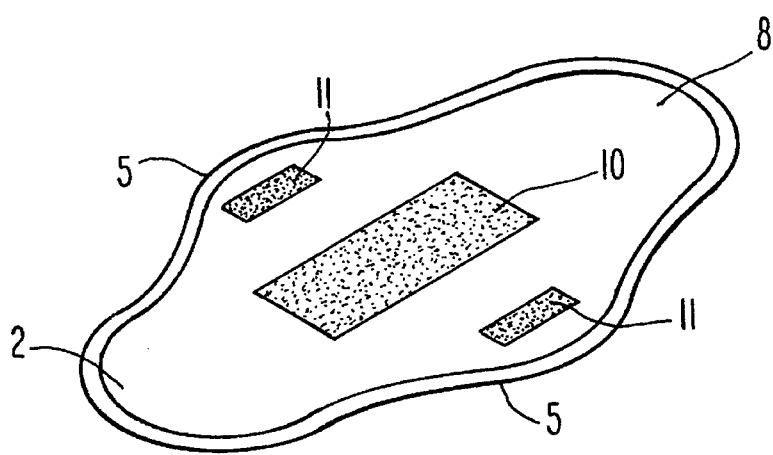
FIG. 3 is an isometric view of the article shown in FIG. 1 ready to be applied to an undergarment.

There is shown in FIGS. 1–3 a sanitary napkin 1 of the type made by the method of the current invention. The napkin 1 is comprised of a longitudinally extending central portion 2 having right and left longitudinal edges 3 and transverse ends 4. In addition, right and left tabs or wings 5 extend laterally from each the longitudinal edges 3.

The construction of the tabbed napkin 1 is shown best in FIG. 3. An absorbent element 7 is disposed in the central portion of the napkin. As is known in the art, the absorbent element 7 may be comprised of a loosely associated absorbent hydrophilic material such as cellulose fibers, wood pulp, regenerated cellulose or cotton fibers, or other absorbent materials generally known in the art, including peat moss or super-absorbent materials.

The side of the napkin that is intended to be worn against the body of the user (i.e., the downward facing side in FIG. 2) is covered by a body-fluid pervious cover 9, which can be any resilient, relatively non-absorbing fluid pervious material. This material is provided for comfort and directs fluid to the underlying element 7 that retains the fluid. The cover should retain little or no fluid in its structure so as to provide a relatively dry surface next to the skin. The fluid pervious cover 9 is preferably a non-woven fabric made of fibers or filaments of thermoplastic polymers such as polyethylene or polypropylene, or an apertured polymeric film. Generally, the fluid pervious cover 8 is a single layer of material having a width sufficient to cover the body-facing side of the napkin.

The napkin 1 further comprises a body fluid impervious barrier 8 on its garment facing side (i.e., the side facing upward in FIGS. 1–3). The impervious barrier 8 may be attached to the pervious cover 9 by heat sealing, by ultrasonic bonding, or by an adhesive. The impervious barrier 8 may comprise any thin, flexible, body fluid impermeable material such as a polymeric film—for example, polyethylene, polypropylene, cellophane—or even a normally fluid pervious material that has been treated to be impervious, such as impregnated fluid repellent paper or non-woven fabric material.

Alternatively, the central portion 2 of the napkin can be formed from an absorbent core 7 having integral body facing and garment facing sides—that is, without separate layers of a body fluid pervious cover 9 and a body fluid impervious barrier 8.

As shown in FIG. 3, the tabs 5 extend laterally from the napkin central portion 2. As shown in FIG. 2, the tabs may be of the integral type formed from a laminate comprised of extensions of the barrier and cover layers 8 and 9, respectively, in the central portion. Alternatively, the tabs 5 may be formed separately and then attached to the central portion 2. Such separately formed tabs are sometimes referred to as "cut and paste" tabs. The tabs 5 may also contain an absorbent (not shown in FIG. 2), such as a tissue layer that has sufficient capillary action to retain small quantities of escaped liquid. This tissue can be heat sealed or adhesively sealed around the edges of the tabs 5 to form absorbent areas.

As shown in FIGS. 2 and 3, a pressure sensitive adhesive patch 10 is applied to the barrier layer 9 on garment facing side of the central portion 2. Additional pressure sensitive adhesive patches 11 are applied to the extensions of the barrier layer 9 that form the garment facing side of each of the tabs 5. In the preferred embodiment, the adhesive patches 10 and 11 may consist of a thermoplastic "hot melt" glue. However, other adhesives may also be utilized, such as acrylate adhesives.

As previously discussed, a release strip 6, shown in FIGS. 1 and 2, is utilized to protect the adhesive patches 10 and 11 prior to use. The release strip 6 is of the double-sided type—that is, the surface on both of its sides adhere to the adhesive patches 10 and 11 with sufficient tenacity to remain in place prior to use but can be readily detached when the napkin is to be used. Such properties may be provided by coating a sheet-like material, such as paper, with a non-stick release agent, such as silicone, that reduces the adherency of the coated side of the release strip to the adhesive as compared the un-coated surface of the release strip.

As shown in FIG. 1, as supplied to the user, the tabs 5 are folded over the central portion 2 to facilitate storage and packaging. In this configuration, the patch of adhesive 10 attaches one side of the release strip 6 to the central portion barrier 9 and the adhesive patches 11 attach the other side of the release strip to the extensions of the barrier layer 8 that form the garment facing sides of the tabs 5.

When the napkin 1 is to be applied to an undergarment, the user must first splay the tabs 5 outward and uncover the adhesive patches 10 and 11, as shown in FIG. 3. As discussed more fully in U.S. Pat. No. 4,701,178 (Glaug), hereby incorporated by reference in its entirety, the use of a single double-sided release strip 6 considerably simplifies this procedure, since a single pull on the release strip both splays the tabs outward and exposes all of the adhesive patches.

After the release strip 6 has been removed, the napkin 1 is applied by placing the garment facing side of the central portion 2 against the inside surface of the crotch of the user's undergarment so that adhesive patch 10 secures the central portion to the crotch. Next, the tabs 5 are folded around the crotch, with the edges of the tabs nearly abutting one another, so that the adhesive patches 11 secure the tabs to the outside surface of the crotch. As so applied, the tabs 5 serve to further stabilize the napkin and prevent side leakage.

Figure 4:
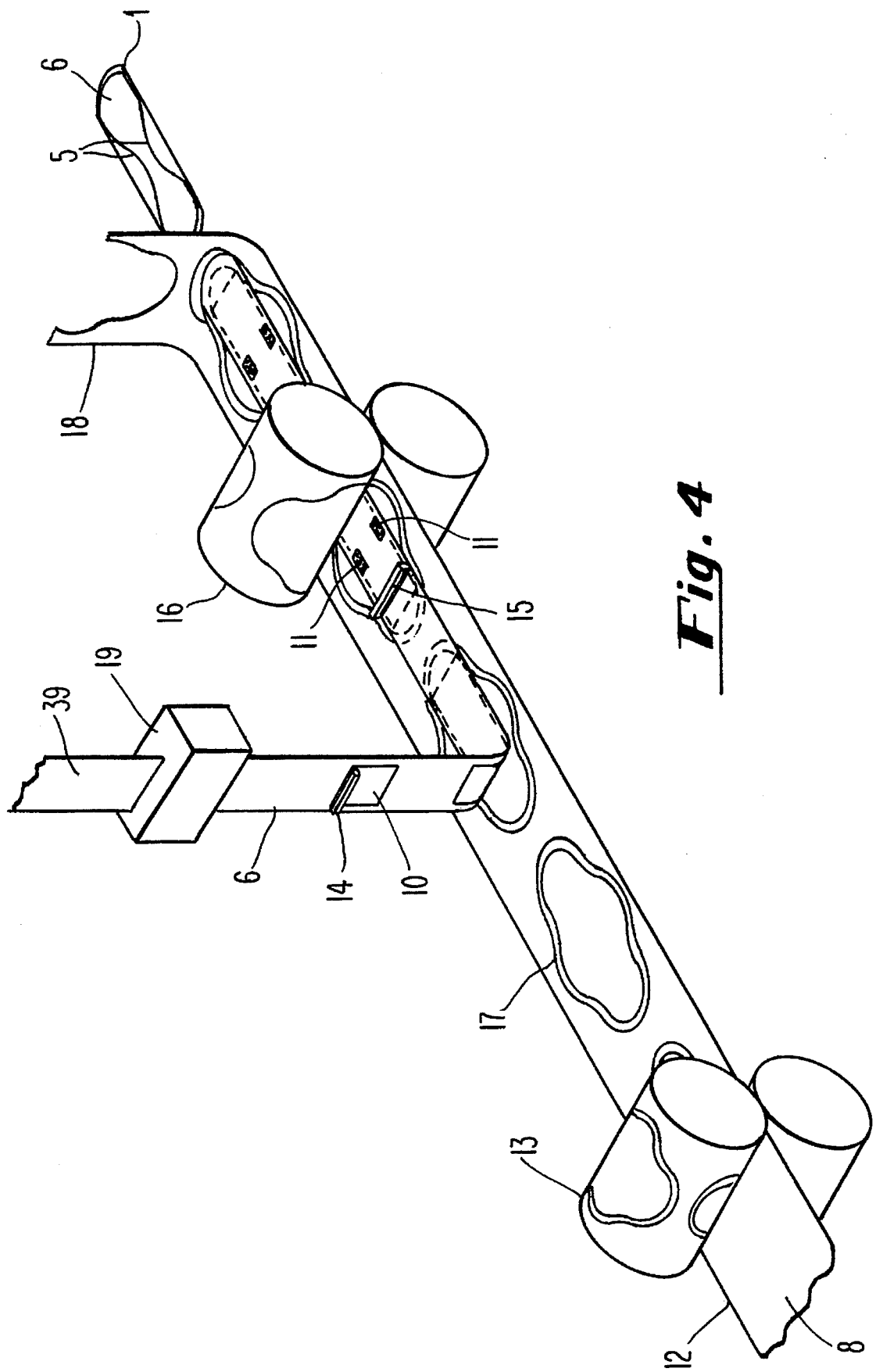
FIG. 4 is a view, partially schematic, of a manufacturing line for making the absorbent article shown in FIG. 1.

A production line for making the napkin 1 is shown in FIG. 4. A strip of laminate 12 is fed to an embosser 13. The laminate strip 12 is formed from layers of the materials used for the cover layer 9 and the barrier layer 8 and is wide enough to cover both the garment facing side of the central portion 2 and the garment facing sides of the tabs 5. In addition, a layer of absorbent 7 material is sandwiched between the barrier and cover layers along the longitudinal centerline of the strip. The laminate strip 12 is fed to the embosser 13 with the barrier layer 8 facing upward. The embosser 13 heat seals the layers of cover 9 and barrier 8 material together along a border 17 that will eventually become the periphery of the napkin 1.

Simultaneously, a strip of paper 39 is fed to a coating unit 19 that applies a release agent, such as silicon, to both sides of the paper, thereby forming a double-sided release strip 6. From the coating unit 19, the release strip 6 is directed to a glue gun 14 where intermittent patches 10 of hot melt adhesive are applied to the lower surface of the strip. Unlike the material forming the barrier layer 8, the release strip 6 is not subject to damaging scorching by the hot glue.

Next, the lower surface of the release strip 6 is place along the center of the layer of barrier 8 material so that the adhesive patches 10 bond the release strip to the barrier layer 8 in the central portion of the napkin. A second glue gun 15 then applies two additional patches 11 of hot melt adhesive along the edges of the release strip 6 on its upper surface. Once again, by applying the hot melt glue directly to the release strip 6, the danger of scorching the barrier layer 8 is avoided.

After the adhesive has been applied, a rotary cutter 16 cuts individual napkins 1 from the laminate strip 12 and the excess laminate 18 is discarded. Lastly, the tabs 5 are folded over the central portion so that the extensions of the barrier layer 8 that form the garment facing side of the tabs 5 contact the upper surface of the release strip 6, thereby bonding the adhesive patches 11 to the tabs.

As a result of both surfaces of the release strip 6 having been covered with a release agent, the adhesive patches 10 and 11 bond more tenaciously to the barrier layer 8 of the central portion 2 and the tabs 5 than they do to the release strip 6 to which they were originally applied. Thus, when the tabs 5 are unfolded by the user by pulling off the release strip 6, as shown in FIG. 3, the adhesive patches 10 and 11 are transferred to the central portion and the tabs, as shown in FIGS. 2 and 3, and the release strip 6 may be discarded. As can be appreciated, in the method according to the current invention, hot melt type adhesive patches 10 and 11 have been applied to the layer of barrier 8 material without incurring the danger of scorching the layer.

A portion of an alternative production line for making tabbed napkins according to the current invention using "cut and paste" tabs is shown in FIG. 5. In this embodiment, a strip of release paper 6 is bonded to a strip of laminate 12' using adhesive patches 10, and its edges heat sealed, as before (not shown). The laminate strip 12' may be essentially the same as the laminate strip 12 previously discussed with respect to the embodiment shown in FIG. 4—that is, layers of cover and barrier material with a layer of absorbent 7 material sandwiched therebetween—except that the width of the laminate strip 12' is no wider than the central portion 2. A glue gun 20 applies patches of construction adhesive 22 along the edges of the laminate strip 12'.

Simultaneously, two strips of tab material 23 are directed to drums 30. The strips 23 may be laminates of the same materials used for the barrier and cover layers 8 and 9. Alternatively, since the tab strips 23 are formed separately from the central portion 2, the tab strips 23 may be formed from laminates of a variety of other materials. In any case, the laminate strips 23 are directed by the drums 30 to a rotary cutter 33 having knife blades 34 that, in conjunction with an anvil 32, cut the strips into individual tabs 5. The tabs 5 are then pressed into the laminate strip 12' so that the patches 22 of construction adhesive bond the base of each tab to the laminate strip.

Next, a second glue gun 21 applies intermittent patches 11 of pressure sensitive adhesive along the edges of the upper surface of the release strip 6, as before. The tabs 5 are then folded over the central portion by a folding apparatus 38—essentially a sheet metal guide with inner surfaces that rotate the tabs around and down onto the release strip 6. In so doing, the tabs 5 contact the upper surface of the release strip 6 so as to bond their tips to the adhesive patches 11. Lastly, the laminate strip 12' is cut into individual napkins (not shown).

When the user pulls off the release strip 6 prior to use, the adhesive patches 10 and 11 are transferred to the central portion 2 and the tabs 5, as before, thereby applying hot melt adhesive patches without incurring the danger of scorching the barrier material.

As the various embodiments disclosed above indicate, the present invention may be embodied in many specific forms without departing from the spirit or essential attributes thereof and, accordingly, reference should be made to the appended claims, rather than to the foregoing specification, as indicating the scope of the invention.

What is claimed is:

1. A method of making an absorbent article comprising at least one laterally extending side tab wherein separate, discrete patches of adhesive are applied to said article and said tab, such method comprising the steps of:

a) forming a central portion having an absorbent element;

b) depositing a first patch of adhesive on a first side of a release strip so that said first patch of adhesive bonds thereto;

c) attaching said release strip to said central portion by placing said first side of the release strip onto said central portion so that said first patch of adhesive bonds to said central portion more tenaciously than said first patch of adhesive bonded to said release strip;

d) depositing a second discrete patch of adhesive on a second side of said release strip so that said second patch of adhesive bonds thereto, the step of depositing said second patch of adhesive being performed after the step of attaching said release strip to said central portion; and e) placing a tab adapted to be folded around a crotch of a user's undergarment onto said second side of said release strip so that said second patch of adhesive bonds to said tab more tenaciously than said second patch of adhesive bonded to said release strip, the step of placing said tab onto said second side of said release strip being performed after the step of depositing said second patch of adhesive on said second side of said release strip;

whereby said first and second patches of adhesive remain on said central portion and said tab, respectively, when said strip is removed from said article.

2. The method according to claim 1, wherein said adhesive comprises a pressure sensitive hot melt glue.

3. The method according to claim 1, further comprising the step of coating said first and second sides of said strip with a second material.

4. The method according to claim 3, wherein said second material is a release agent that causes said first and second patches of adhesive to preferentially bond with greater tenacity to said central portion and said tab, respectively, than to said first and seconds sides of said strip.

5. The method according to claim 3, wherein said second material comprises a silicone coating.

6. The method according to claim 1, wherein the step of forming said central portion comprises the step of enclosing at least a portion of said absorbent element with a layer of a second material, and further comprising the step of forming said tab from said layer of second material.

7. The method according to claim 6, wherein the step of placing said tab on said second side of said strip further comprises the step of placing said tab so that said second patch of adhesive bonds to said layer of second material.

8. The method according to claim 6, wherein said central absorbent has a longitudinal side, and wherein the step of forming said central portion comprises the step of enclosing at least a portion of said absorbent element with a layer of said second material so that a portion of said layer of second material extends beyond said longitudinal side, and wherein the step of forming said tab from said portion of said layer of second material comprises forming said tab from said portion of said layer of second material extending beyond said longitudinal side.

9. The method according to claim 8, wherein the step of placing a tab on said second side of said strip comprises the step of folding said tab over said central portion.

10. The method according to claim 1, wherein said tab comprises a layer of a second material, and wherein the step of placing said tab on said second side of said strip further comprises the step of placing said tab so that said second patch of adhesive bonds to said layer of second material.

11. The method according to claim 10, wherein said second material is formed from a polymeric film.

12. A method of making an absorbent article comprising at least one side tab wherein separate, discrete patches of adhesive are applied to said article and said tab, such method comprising the steps of:

a) forming a central portion by covering an absorbent element with a layer of material so that a first portion of said layer extends laterally right and left from said central portion, thereby forming right and left tabs adapted to wrap around a crotch of a user's undergarment;

b) depositing a first patch of adhesive on a first side of a double-sided release strip so that said first patch of adhesive bonds thereto;

c) placing said first side of said release strip on said first portion of said layer of material after said first patch of adhesive has been deposited on said first side of said release strip so that said first patch of adhesive bonds to said layer of material with greater tenaciously than said first patch of adhesive bonds to said release strip;

d) depositing a second patch of adhesive on a second side of said release strip after said release strip has been placed on said first portion of said layer of material so that said second patch of adhesive bonds thereto; and e) folding said tabs over said second side of said release strip after said second patch of adhesive has been deposited on said second side of said release strip so that said second patch of adhesive bonds to said first portion of said layer that forms said tabs with greater tenaciously than said second patch of adhesive bonded to said release strip;

whereby said first and second patches of adhesive remain on said central portion and said tab, respectively, when said strip is removed from said article.

13. The method according to claim 12, wherein said adhesive is a pressure sensitive hot melt glue.

14. The method according to claim 13, wherein said layer of material is formed from a polymeric film.

15. In a method of making an absorbent article comprising a tab extending from a central portion, wherein separate, discrete patches of adhesive are applied to said article and said tab, a method of applying adhesive to said tab for attaching said tab to a user's undergarments, comprising the steps of:

a) attaching a first side of a double-sided release strip to a central portion having an absorbent;

b) depositing an adhesive on a second side of said release strip after said release strip has been attached to said central portion so that said adhesive bonds thereto; and c) transferring said adhesive to said tab by placing said tab against said second side of said release strip after said adhesive has been deposited onto said second side of said release strip so that said adhesive bonds to said tab, whereby when said release strip is detached from said central portion said adhesive preferentially remains bonded to said tab rather than to said release strip.

16. The method according to claim 15, wherein said adhesive is a hot melt glue.

17. The method according to claim 16, wherein:

a) said tab is comprised of a layer of material formed from a polymeric film; and b) the step of transferring said adhesive to said tab comprises the step of placing said layer of material against said second side of said release strip so that said adhesive bonds to said polymeric film.

* * * * *